United States Patent
Silveri

(10) Patent No.: US 8,298,391 B2
(45) Date of Patent: Oct. 30, 2012

(54) AMPEROMETRIC SENSOR

(76) Inventor: Michael A. Silveri, Incline Village, NV (US)

( * ) Notice: Subject to any disclaimer, the term of this patent is extended or adjusted under 35 U.S.C. 154(b) by 1001 days.

(21) Appl. No.: 12/167,171

(22) Filed: Jul. 2, 2008

(65) Prior Publication Data

US 2009/0014329 A1    Jan. 15, 2009

Related U.S. Application Data

(60) Provisional application No. 60/949,201, filed on Jul. 11, 2007.

(51) Int. Cl.
*G01N 27/26* (2006.01)
*C02F 1/76* (2006.01)
*C02F 1/461* (2006.01)

(52) U.S. Cl. ............. 204/416; 210/754; 210/748.2; 204/228.6; 204/400; 204/412

(58) Field of Classification Search ............ 204/412, 204/433, 416, 405, 406, 400, 228.6; 205/778.5, 205/789; 210/739, 754, 748.2
See application file for complete search history.

(56) References Cited

U.S. PATENT DOCUMENTS

| | | | |
|---|---|---|---|
| 3,776,832 A * | 12/1973 | Oswin et al. | 240/411 |
| 3,975,271 A | 8/1976 | Saunier et al. | |
| 4,033,830 A | 7/1977 | Fletcher, III | |
| 4,224,154 A | 9/1980 | Steininger | |
| 4,427,772 A | 1/1984 | Kodera et al. | |
| 4,808,287 A * | 2/1989 | Hark | 210/637 |
| 4,992,156 A | 2/1991 | Silveri | |
| 5,019,250 A | 5/1991 | Lorenzen | |
| 5,221,444 A | 6/1993 | Silveri | |
| 5,240,228 A | 8/1993 | Silveri | |
| 5,251,656 A | 10/1993 | Sexton, Sr. | |
| 5,320,748 A | 6/1994 | Dupuis | |
| 5,331,966 A | 7/1994 | Bennett et al. | |
| 5,359,769 A | 11/1994 | Silveri | |
| 5,389,210 A | 2/1995 | Silveri | |
| 5,401,373 A | 3/1995 | Silveri | |
| 5,422,014 A | 6/1995 | Allen et al. | |
| 5,441,073 A | 8/1995 | Hoadley | |
| 5,545,310 A | 8/1996 | Silveri | |

(Continued)

FOREIGN PATENT DOCUMENTS

WO    2006007533 A1    1/2006

OTHER PUBLICATIONS

Innovation News 2001 article showing the Censar has been around since at least 2001. Also see Censar overview document.*

(Continued)

*Primary Examiner* — Jeffrey T Barton
*Assistant Examiner* — Jennifer Dieterle
(74) *Attorney, Agent, or Firm* — Jerry Turner Sewell

(57) ABSTRACT

An amperometric sensor includes a first electrode, a second electrode and a reference electrode. The sensor further includes a switch to selectably electrically connect the first electrode as a working electrode and to electrically connecting the second electrode as an auxiliary electrode during a first time interval. During a second time interval, the switch electrically connects the first electrode as the auxiliary electrode and electrically connects the second electrode as the working electrode. The switching of the two electrodes is repeated continuously as amperometric measurements are performed. Preferably, the sensor includes an ultrasonic transducer proximate the working electrode and the auxiliary electrode to clean the electrodes.

1 Claim, 6 Drawing Sheets

U.S. PATENT DOCUMENTS

| | | | |
|---|---|---|---|
| 5,580,438 | A | 12/1996 | Silveri |
| 5,616,239 | A | 4/1997 | Wendell et al. |
| 5,676,805 | A | 10/1997 | Silveri |
| 5,752,282 | A | 5/1998 | Silveri |
| 5,759,384 | A | 6/1998 | Silveri |
| 5,885,426 | A | 3/1999 | Silveri |
| 5,932,093 | A | 8/1999 | Chulick |
| 6,007,693 | A | 12/1999 | Silveri |
| 6,123,839 | A | 9/2000 | Sussman |
| 6,125,481 | A | 10/2000 | Sicilano |
| RE37,055 | E | 2/2001 | Silveri |
| 6,182,681 | B1 | 2/2001 | Robertson et al. |
| 6,238,555 | B1 | 5/2001 | Silveri et al. |
| 6,270,680 | B1* | 8/2001 | Silveri et al. ............ 210/746 |
| 6,309,538 | B1 | 10/2001 | Khan |
| 6,340,431 | B2 | 1/2002 | Khan |
| 6,536,272 | B1 | 3/2003 | Houston et al. |
| 7,056,664 | B1* | 6/2006 | Hartwich et al. ............ 435/6.12 |
| 7,189,314 | B1* | 3/2007 | Pace et al. ............ 204/412 |
| 2001/0004962 | A1* | 6/2001 | Hirota et al. ............ 204/228.1 |
| 2001/0016682 | A1 | 8/2001 | Berner et al. |
| 2002/0014410 | A1* | 2/2002 | Silveri et al. ............ 204/412 |
| 2002/0070112 | A1* | 6/2002 | Lee et al. ............ 204/431 |
| 2002/0116042 | A1 | 8/2002 | Boling |
| 2004/0138840 | A1 | 7/2004 | Wolfe |
| 2004/0211731 | A1* | 10/2004 | Ferguson et al. ............ 210/739 |
| 2006/0144704 | A1* | 7/2006 | Ghesquiere et al. ..... 204/403.01 |
| 2008/0017523 | A1 | 1/2008 | Dietze |

OTHER PUBLICATIONS

Censar overview document of Censar probe.*

ISA/US, "PCT Notification of Transmittal of the International Search Report and the Written Opinion of the International Searching Authority, or the Declaration"; "PCT International Search Report"; and "PCT Written Opinion of the International Searching Authority" for International Application No. PCT/US2008/069255, Nov. 20, 2008, 10 pages total.

The International Bureau of WIPO, Authorized Officer Masashi Honda, "PCT Notification Concerning Transmittal of International Preliminary Report on Patentability (Chapter I of the Patent Cooperation Treaty," Form PCT/IB/326, for International Application No. PCT/US2008/069255, Jan. 21, 2010, 1 page.

The International Bureau of WIPO, Authorized Officer Masashi Honda, "PCT International Preliminary Report on Patentability (Chapter I of the Patent Cooperation Treaty)," Form PCT/IB/373, for International Application No. PCT/US2008/069255, Jan. 12, 2010, 6 pages.

* cited by examiner

AMPEROMETRIC SENSOR

BACKGROUND OF THE INVENTION

1. Field of the Invention

The present invention relates generally to systems for testing water chemistry, and, more particularly, relates to amperometric sensors.

2. Description of the Related Art

A need exists for a simple, reliable long life chlorine (or bromine) measurement system that can also measure both high levels of chlorine (or bromine) and low levels of chlorine (or bromine) with high accuracy over a wide range of levels. The system should also operate reliably in conditions that may cause scaling and that may result in biofouling of the sensor.

A common problem encountered with online measurement of chlorine or bromine in the field is fouled electrodes. Electrodes measurements can be rendered unreliable when the working electrode is covered with either inorganic (salts such as calcium carbonate) layers or organic (biofouling) layers that inhibit electrode processes.

Pulsing techniques are often used to clean the electrodes to provide repeatable measurements. Some examples of pulsing techniques are shown in U.S. Pat. No. 6,238,555 for Amperometric Halogen Control System and in U.S. Pat. No. 6,270,680 for Amperometric Sensor Probe for an Automatic Halogen Control System. While pulsed techniques are widely used, problems arise when using this method with certain electrode materials and when used in online control systems for water treatment. For example, gold works well as a working electrode in a chlorine measurement system. To clean the working electrode, a positive pulse greater than 1 volt must be applied to generate protons to clean salts from the surface. To merely achieve oxidation on the surface, a DC potential of 0.7 volts or more must be applied with respect to an Ag/AgCl electrode. This potential is very near the potential at which the gold electrode may be damaged from irreversible oxide formation.

Another disadvantage of pulsed techniques is the frequency of the measurement. Since several minutes of pulsing and stabilization are typically required, many minutes may elapse between measurements. While not an issue in slowly responding systems such as a swimming pool, this time may be unacceptably long for municipal water systems or in a hot tub or commercial spa.

Censar Technologies, Inc., (a unit of Siemens AG) uses a replaceable thin-film sensor formed on a substrate with multiple electrodes. The sensor has a very short life of approximately 6 months. The embodiments in accordance with aspects of the invention disclosed herein use novel circuitry to use the chlorine measurement electrodes for multiple measurements. The use of the novel circuitry results in a robust, reliable sensor that is lower in cost than the Censar approach. See, for example, U.S. Pat. No. 5,483,164 to Moss et al.

Another system uses an impeller to move cleaning balls that abrade the surface of the electrode.

Other systems use a fixed potential to measure chlorine. These systems usually take 24 hours or more to stabilize and are subject to fouling and frequent calibration.

Membrane sensors operate reliably in drinking water applications but often foul under conditions that include high levels of organics or other contaminants. Membrane sensors require frequent maintenance and recalibration and cannot be used in high pressure applications.

Oxidation reduction potential (ORP) is a method that is commonly used in swimming pools as a substitute for chlorine control. This method has a number of deficiencies including non-specificity. The ORP method measures the sum total of all redox couples in the water, not just chlorine. The method exhibits a logarithmic response to the chlorine level and is easily poisoned by organics, including cyanuric acid, a chemical that can easily reach excessive levels in swimming pools. Reports of levels as high as 350 ppm are common. When such high levels are reached, ORP sensors reportedly must be cleaned every three days.

While the ORP method is not always the best choice for a chlorine controller, the method can be used as a qualitative indicator of water quality and works well in some process applications.

Keeping amperometric sensors clean (e.g., avoiding scale build up) is an issue with water chemistry measurement systems. Ultrasonic energy is widely used for cleaning applications. Wissenschaftlich-Technische Werkstaetten GmBH (WTW) of Weilheim, Germany, sells an ultrasonically cleaned optical sensor for wastewater suspended solids measurement, such as, for example, the sensor disclosed in U.S. Pat. No. 6,678,045. An ultrasound generating transducer is built into the sensor tip. The transducer is electronically activated to produce ultrasonic waves in the electrodes. In ultrasonic cleaning, the main mechanism of cleaning action is by energy released from the creation and collapse of microscopic cavitation bubbles, which break up and lift off dirt and contaminants from the surface to be cleaned.

Ultrasonic transducers work by rapidly changing size when excited by an electrical signal. This creates a compression wave in the liquid. The compression waves actually "tear" the liquid apart, leaving behind a "void" or "partial vacuum bubble." When these "bubbles" (e.g., millions of bubbles) collapse, enormous energy is produced. When sufficient energy is built up in the "bubble" or cavitation, the cavitation collapses violently.

Another known system available from Emerson Process Management utilizes a separate chamber into which a conventional pH sensor can be inserted. Water flows through the chamber and ultrasonic energy is applied the chamber wall. This device is extremely expensive and uses very high voltages (greater than 500 volts). Since the energy is applied to the water instead of directly applying it to the electrodes, the device is both cumbersome and inefficient.

SUMMARY OF THE INVENTION

Embodiments in accordance with the invention disclosed herein operate with alternating cycles of opposite polarity. At the end of each cycle, the polarity of the voltages applied to the working electrode and the auxiliary electrode reverse to effectively swap the positions of the working electrode and the auxiliary electrode. In particular, the positions of the working electrode and the auxiliary electrode in the circuit are swapped such that a first electrode that was the working electrode in a first cycle becomes the auxiliary electrode in a second cycle, and a second electrode that was the auxiliary electrode in the first cycle becomes the working electrode in the second cycle. Reversing the electrodes effectively reverses the current flowing through the electrodes. Since the current flows in opposite directions through the electrodes in alternating cycles, the embodiments disclosed herein do not build up scale that tends to build up in systems where the working electrode and the auxiliary electrode are always connected in the same electrical position.

Since swapping the electrode positions on alternating measurement cycles prevents scale from building up on the electrodes, embodiments in accordance with the present invention do not apply high damaging potentials to the electrodes. Furthermore, the disclosed embodiments enable measurements to be made while the other electrode is depolarized.

The embodiments described herein also employ redundancy with respect to the working electrode. If the same measured values are not received for both positions of the electrodes, a fault may be present and a warning can be displayed.

The conventional approach in analytical chemistry is to use an auxiliary electrode that is 5 to 10 times the size of the working electrode to ensure that the reaction at the working electrode is not limited by the auxiliary electrode. However, in the embodiments described herein, such a large auxiliary electrode is unnecessary. Even at very high currents, the sensor disclosed herein exhibits a nearly linear response so that both electrodes can be generally the same size.

Platinum and gold work well in the disclosed embodiments and provide a consistent surface finish when plated electrodes are used. Plated electrodes are also much easier to manufacture than are solid precious metal electrodes.

In one illustrated embodiment, the circuit positions of the first and second electrodes are swapped using a relay or other suitable switching device. After one or two minutes in each circuit position, measurements are made, and the measured signal is averaged during the last few seconds. The calibration for zero at each position is stored as well as the individual slope for each electrode. An algorithm checks the measurements for both circuit positions and displays a fault if the two measurements deviate by more than a preset level. The average of both signals is displayed.

The electrodes are symmetric and are preferably made from the same materials. In a clean system, the polarity reversal technique disclosed herein is sufficient to avoid scale buildup, thus avoiding a need for a separate cleaning mechanism.

This method disclosed herein may be used with a pH electrode. The reference portion of the combination sensor can be used advantageously for both the chlorine circuit and the pH circuit. The embodiment disclosed herein uses a replaceable pH sensor in the assembly. Alternatively, a chlorine-only sensor may be built using either a gelled reference electrode or a solid state reference electrode.

In certain embodiments, the sensor may also be cleaned using an ultrasonic cleaning device, which has the advantage of cleaning the reference electrode as well as the chlorine electrodes in contrast to a pulsing system, which will not clean the reference electrode.

A combination pH sensor may advantageously be included in the system if pH measurements are required or if very tight control of chlorine is needed (pH affects the chlorine signal). The reference electrode of the pH sensor is used as the reference electrode for the amperometric chlorine, pH and oxidation reduction potential (ORP) measurements. If pH is not needed, a solid state reference electrode may be used in place of the pH sensor. This reduces the cost and increases the reliability since pH electrodes have a relatively short life. When the solid state reference electrode is used, the ultrasonic cleaning methods described later can be used on this electrode as well.

The disclosed embodiments advantageously provide "differential pH measurement." Instead of using an earth ground for the pH measurement circuitry, the chlorine auxiliary electrode is used as the solution ground during the pH measurement. This eliminates the possibility of stray currents damaging the reference electrode or interfering with the measurement accuracy. Previously, expensive pH electrodes with their own internal ground were required for this type of measurement. The embodiments disclosed herein use a low cost, standard pH electrode to accomplish a similar result.

For added redundancy, and as an additional water quality parameter, ORP measurement can also be added to the disclosed system. Measuring the potential between the auxiliary (gold) electrode and the reference electrode provides an ORP signal that can be compared to the chlorine level. If the chlorine level is low (e.g., 0) but the ORP is high (e.g., >700 millivolts this may indicate a problem with the system.

Another redundancy check compares the signal at both working electrodes. If the two signals are not within 10% of each other, a problem may be indicated.

This method of ORP has a number of advantages over conventional ORP systems. For example, the electrodes are maintained in a clean condition rather than having to be cleaned periodically. Furthermore, poisoning of the electrodes is substantially eliminated.

An additional redundancy check is provided by the auxiliary voltage window. The auxiliary voltage with respect to the voltage on the reference electrode is monitored during the chlorine measurement. Monitoring the auxiliary voltage can indicate a problem with the working electrode.

The chlorine measurement circuit is used to measure conductivity sequentially. Sequential measurement of conductivity reduces cost as well as the number of components, thus increasing the reliability of the system. The chlorine measurement circuit enables compensation of the chlorine level based on the conductivity of the solution to lessen the need for user calibration in different water sources. The chlorine measurement circuit also enables an indication of salt level when used to control a chlorine generator. The chlorine measurement circuit also provides an indication of the presence of air in the system. Furthermore, the chlorine measurement circuit, conditions the chlorine sensor for measurement.

A 1 megohm digital potentiometer in the current-to-voltage converter allows a wide range of input current for measuring sanitizer levels. The sensitivity will be increased until the signal is roughly 50 to 75% of the full scale to provide maximum sensitivity. Adjusting the input current can also be used to calibrate or check the calibration of the chlorine sensor in certain embodiments of a chlorine dosing system.

By measuring sanitizer levels during addition of concentrated chlorine and by placing the sensor in series with the chlorine source, a level of concentrated chlorine can be estimated. This estimate serves as an indicator that the source of chlorine is adequate and that the sensor is responding properly to increased chlorine levels.

The potentiometer is set at its minimum resistance at the start of the measurement. If the conditions of saturation remain constant and if the temperature is known, the calibration of the sensor can be checked. The sensitivity may also be recalculated. At the very least, this initial step can serve as a means of verification that the sensor is responding to chlorine.

When using gold electrodes, the ideal measurement potential is within the range of 0.0 volts to 0.4 volts with respect to the voltage on an Ag/AgCl reference electrode. The preferred potential difference is approximately 0.2 volts. Measured currents at zero chlorine level are virtually zero indicating that there is no interference from dissolved oxygen that was measured at roughly 8 milligrams/liter.

BRIEF DESCRIPTIONS OF THE DRAWINGS

DETAILED DESCRIPTION OF PREFERRED EMBODIMENTS

Figure 1:
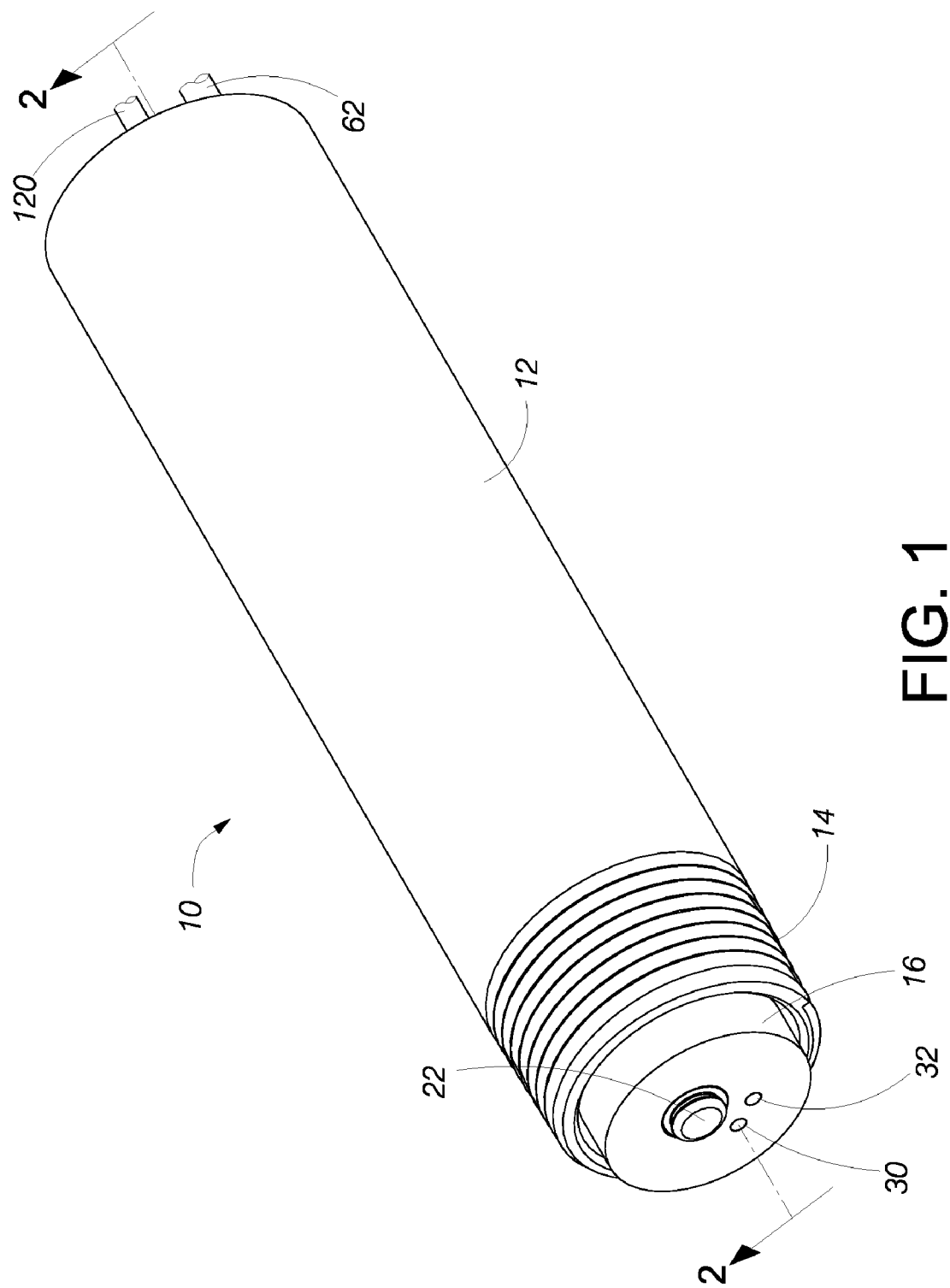
FIG. 1 illustrates a perspective view of an exemplary combination amperometric measurement probe and pH probe.
Figure 2:
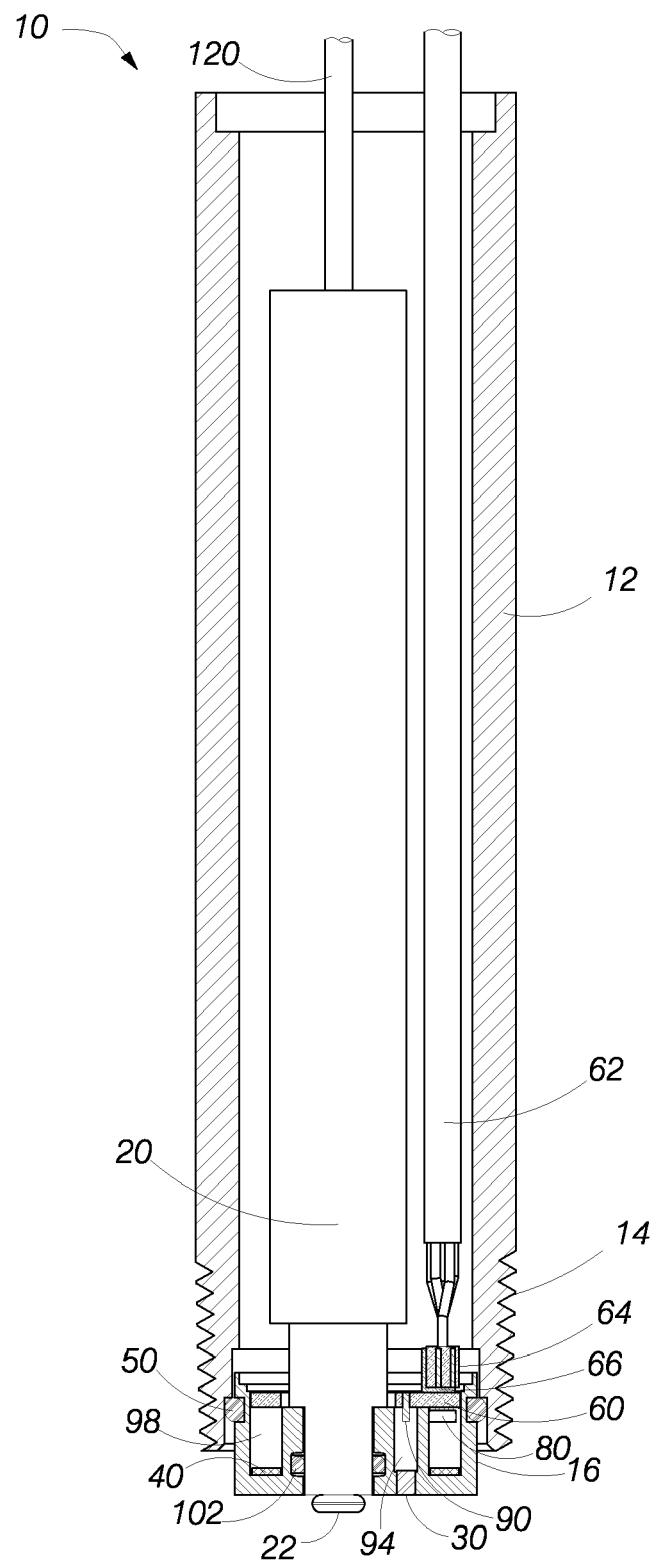
FIG. 2 illustrates a partial cross-sectional view of an exemplary combination amperometric measurement probe and pH probe taken along the line 2-2 in FIG. 1.
Figure 3:
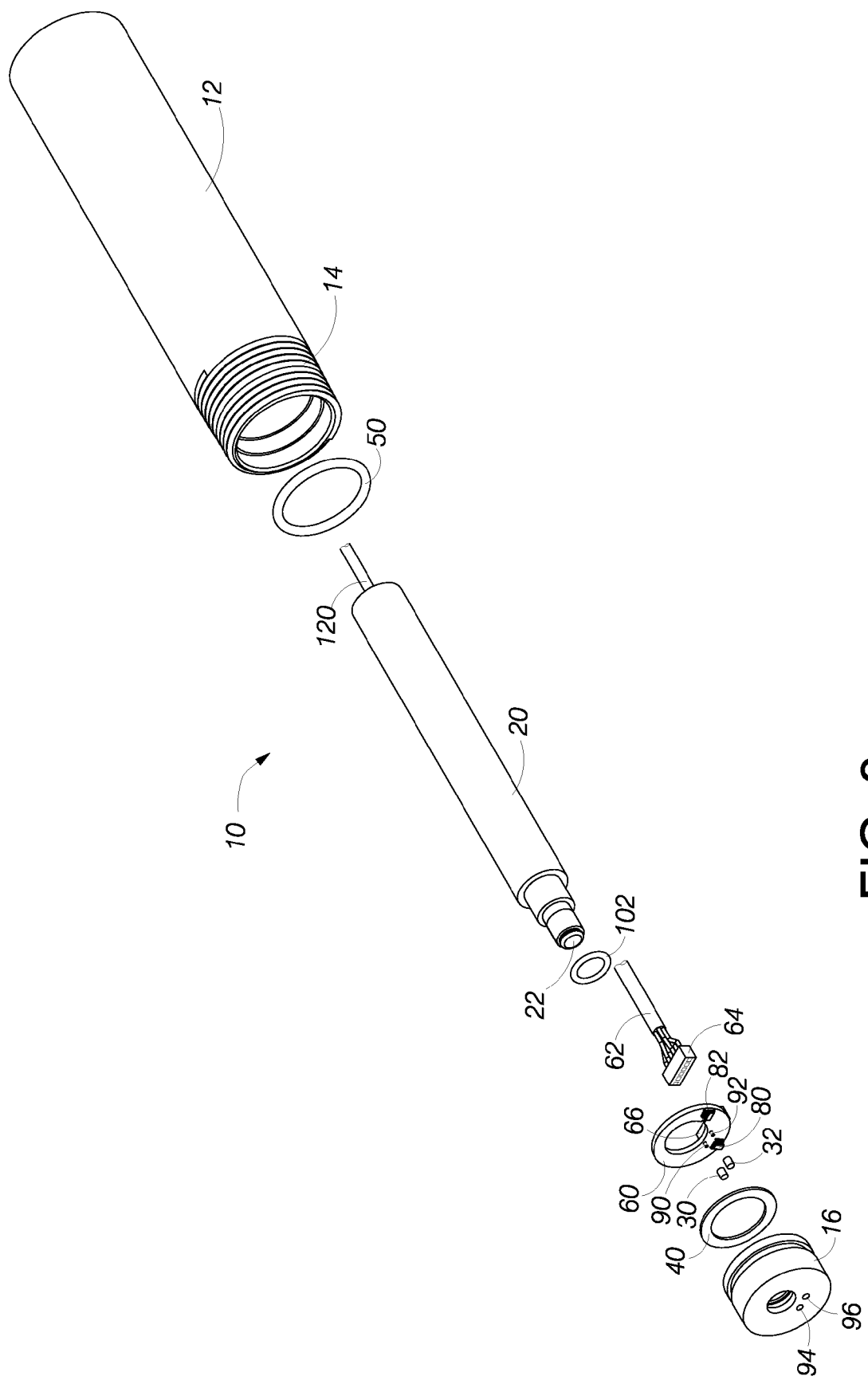
FIG. 3 illustrates an exploded perspective view of the probe of FIG. 1.
Figure 4:
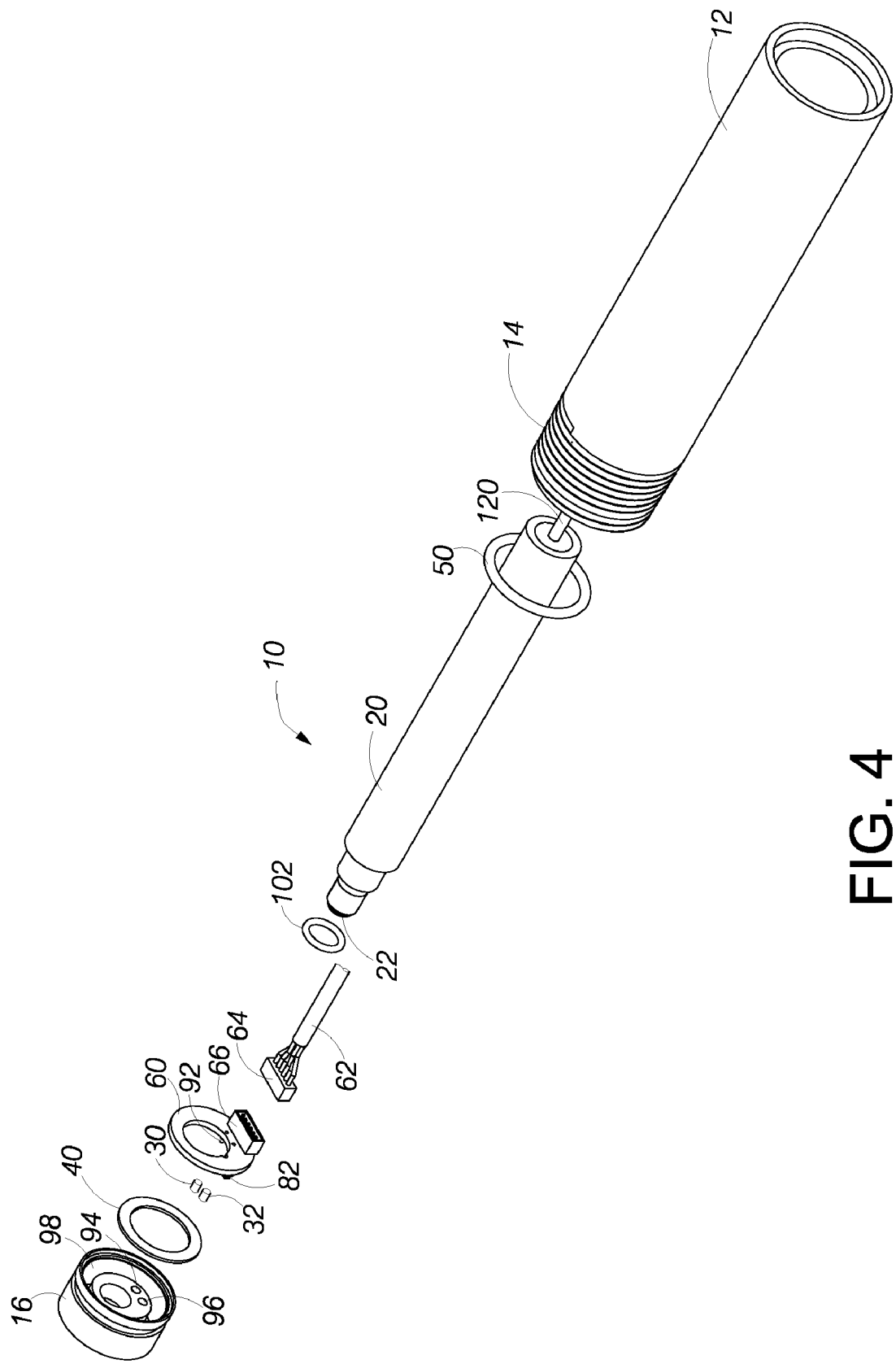
FIG. 4 illustrates an exploded perspective view of the probe of FIG. 1 looking in the opposite direction from the direction in FIG. 3.

Embodiments are disclosed herein with respect to the measurement of the concentration of chlorine in water. It should be understood that the disclosed embodiments are adaptable to the measurement of the concentration of bromine.

As shown in FIGS. 1-4, a sensor 10 is housed in a conduit 12 such as a conventional one-inch pipe nipple having a threaded end 14 that is engagable with a water line (not shown) in a hot tub, a spa or other water feature having a water chemistry that needs to be monitored. When engaged with a water line (e.g., via engagement with internal threads in a tee in the water line), a tip 16 of the sensor 10 extends from the threaded end 14 of the conduit 12 and is surrounded by water in the water line. Alternatively, a twist lock construction may be used to simplify replacement of the sensor and to enable the sensor tip to be relocated with respect to water flows and water levels.

The sensor tip 16 seals the end of the conduit 12, supports an active end 22 of a ph sensor 20 and supports the first electrode 30 and the second electrode 32 of an amperometric sensor (e.g., a chlorine sensor). The sensor tip 16 also supports an ultrasonic transducer (e.g., a piezoelectric crystal) 40. The sensor tip 16 comprises a material selected to provide efficient transmission of ultrasonic energy from the piezoelectric crystal to the electrodes with minimum attenuation. A low durometer (40 Shore A) O-ring 50 also minimizes attenuation with the sensor housing 12 while providing a seal between the sensor tip 16 and the solution in which the sensor tip 16 is inserted. The ultrasonic energy from the piezoelectric crystal 40 may be applied continuously to the electrodes without adversely affecting the measurement. The piezoelectric crystal 40 may also be operated intermittently (e.g., only between measurements).

This sensor tip 16 effectively and efficiently transmits ultrasonic energy to the measurement electrodes 30, 32 in the chlorine sensor as well as to the integral pH sensor 20 or to a reference electrode (not shown) if no pH sensor is present. When used with a pH sensor, the pH sensor 20 may be bonded or welded to the sensor tip 16 or may be an integral part of the sensor tip (same plastic part) to increase the energy that reaches the pH sensor.

The voltage applied to the ultrasonic transducer 40 is an AC voltage, or square wave voltage, on the order of 25 volts to 200 volts. Multiple transducers can be driven in parallel to increase the ultrasonic energy applied to the sensor tip. The one or more transducers 50 are epoxy bonded to the sensor tip. Wires are soldered to the one or more piezoelectric crystals that comprise the transducers 40. The transducers 40 operate over a frequency range from about 40 kHz to about 250 kHz. The frequency varies with each transducer as well as with the type of transducer (e.g., ring transducers versus disc transducers). Each transducer 40 has one or more resonant points. To ensure that each transducer is driven at the transducer's respective resonant point, the frequency applied to the transducers may be swept repeatedly over a narrow range of frequencies. When ultrasonic sensor cleaning is used in combination with the embodiments described herein, power levels of the magnitude described in U.S. Pat. No. 6,678,045 are not generally required; however, increased energy may be necessary in some waters.

Figure 7:
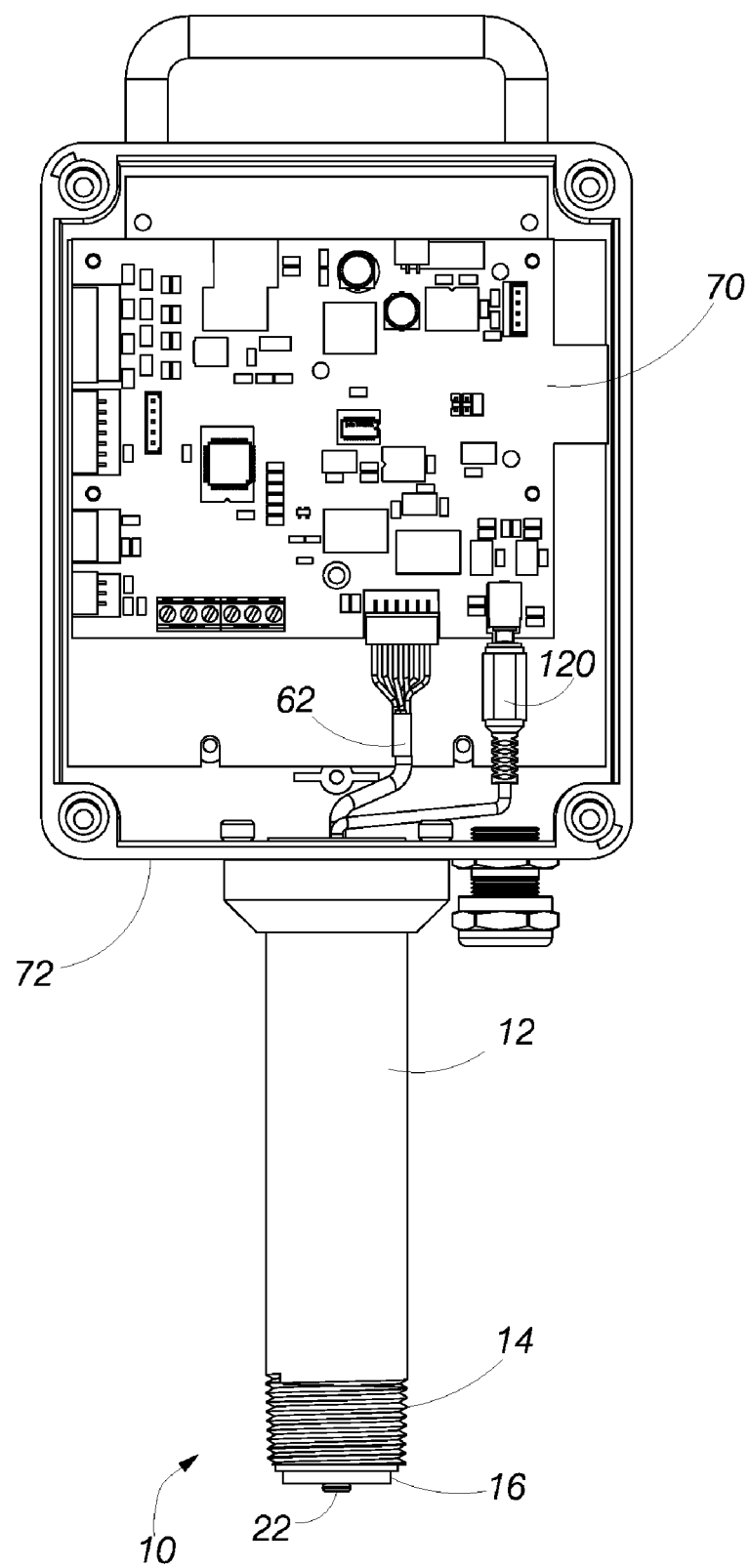
FIG. 7 illustrates a waterproof control box for housing the control circuitry of FIG. 5 and showing the probe of FIGS. 1-4 extending from the control box.

In the illustrated embodiment, the sensor tip 16 houses a sensor printed circuit board (PCB) 60 that is used to make electrical contact with the measurement electrodes 30, 32 and with conductors 62 that extend from a connector 64 that engages with a header 66 on the PCB through the conduit 12 to a main circuit board 70 (a portion of which is shown schematically in FIG. 5) in a control housing 72 (shown in FIG. 7). An electrically erasable programmable read-only memory (EEPROM) 80 on the PCB 60 stores the calibration for both the pH sensor 20 and the chlorine sensor (electrodes 30, 32). Preferably, the sensor tip 16 includes an optional temperature sensor 82 that is also used to compensate the pH and conductivity readings. Both the temperature sensor and the EEPROM 80 are packaged in standard SOT23-6 (6-pin, dual-in-line) packages. The temperature sensor 82 and the EEPROM 80 are placed on the opposite side of the PCB from the header 64 so that the two components can be epoxy potted into the sensor tip. Accordingly, the temperature sensor 82 will remain at substantially the same temperature as the electrodes 30, 32.

Two jumpers 90, 92 connect the PCB 60 to the first electrode 30 and to the second electrode 32. The jumpers protrude from the PCB 60 and extend into electrode cavities (94, 96) within a larger cavity 98 in the sensor tip 16. The electrode cavities 94, 96 for the first electrode 30 and the second electrode 32 are pressed into place from the inside of the sensor tip 16 and are pressed flush with the end of the sensor tip 16. An interference fit provides a water tight seal against the outer walls of the electrode cavities. The electrode cavities 94, 96 are filled with conductive epoxy to complete the electrical connection from the jumper wires 90, 92 to the first electrode 30 and the second electrode 32, which extend from the cavities and protrude from the sensor tip 16 into the water in the water line (not shown). After completing the electrical connections in the electrode cavities, the larger cavity 98 is filled with non-conductive epoxy to seal the electrical connections.

The pH electrode 20 is used for pH measurement. The pH electrode 20 includes an integral reference electrode (not shown). The reference electrode of the pH electrode 20 is also used for chlorine measurement. The reference electrode is a double-junction electrode with a gelled reference in the upper and lower chambers. The reference junction is made from a Pellon® paper (non-woven interface material), which allows wicking of the electrolyte from one chamber to another and from the lower chamber to the water and completes the circuit between the reference electrode in the upper chamber and the water.

The first measurement electrode 30 and the second measurement electrode 32 comprise titanium and are plated or coated with a conductive catalytic material such as, for example, gold or platinum. The two measurement electrodes 30, 32 have diameters that range from approximately 0.06 inch (1/16 inch) to approximately 0.125 inch (1/8 inch), and each electrode has a plating or coating with a thickness of approximately 1 micron to approximately 7 microns. Alternatively, one or both of the electrodes may comprise a solid gold rod.

The tip 22 of the pH sensor 20 fits in a smaller counterbore 100 of the sensor tip 16. An O-ring seal 102 is positioned against the smaller counterbore 100 and the sensor tip 22 to enable replacement of the pH sensor 20 without replacing the entire sensor 10. For example, the gelled reference electrode within the pH sensor 20 depletes over time and usually fails before the other components in the sensor 10.

As indicated above, the sensor tip 16 comprises a material selected to provide efficient transmission of ultrasonic energy from the piezoelectric crystal to the electrodes with minimum attenuation. Preferably, the sensor tip 16 comprises a hydrophobic material such as, for example, a polyetheretherketone (PEEK), polychlorotrifluorethyene (KEL F) or Ultra High Molecular Weight Polyethylene. In particularly preferred embodiments, the sensor tip 16 comprises 30% glass-filled Ultem® (amorphous polyetherimide thermoplastic resin from General Electric).

In the illustrated embodiment, the pH sensor 20 is coupled to the main circuit board 70 via a pH cable 120, which comprises a shielded cable that is separate from the sensor cable 62. The separate pH cable 120 enables replacement of the pH sensor 20 with the integral reference electrode separately from the chlorine/temperature portion of the sensor 10.

Figure 5:
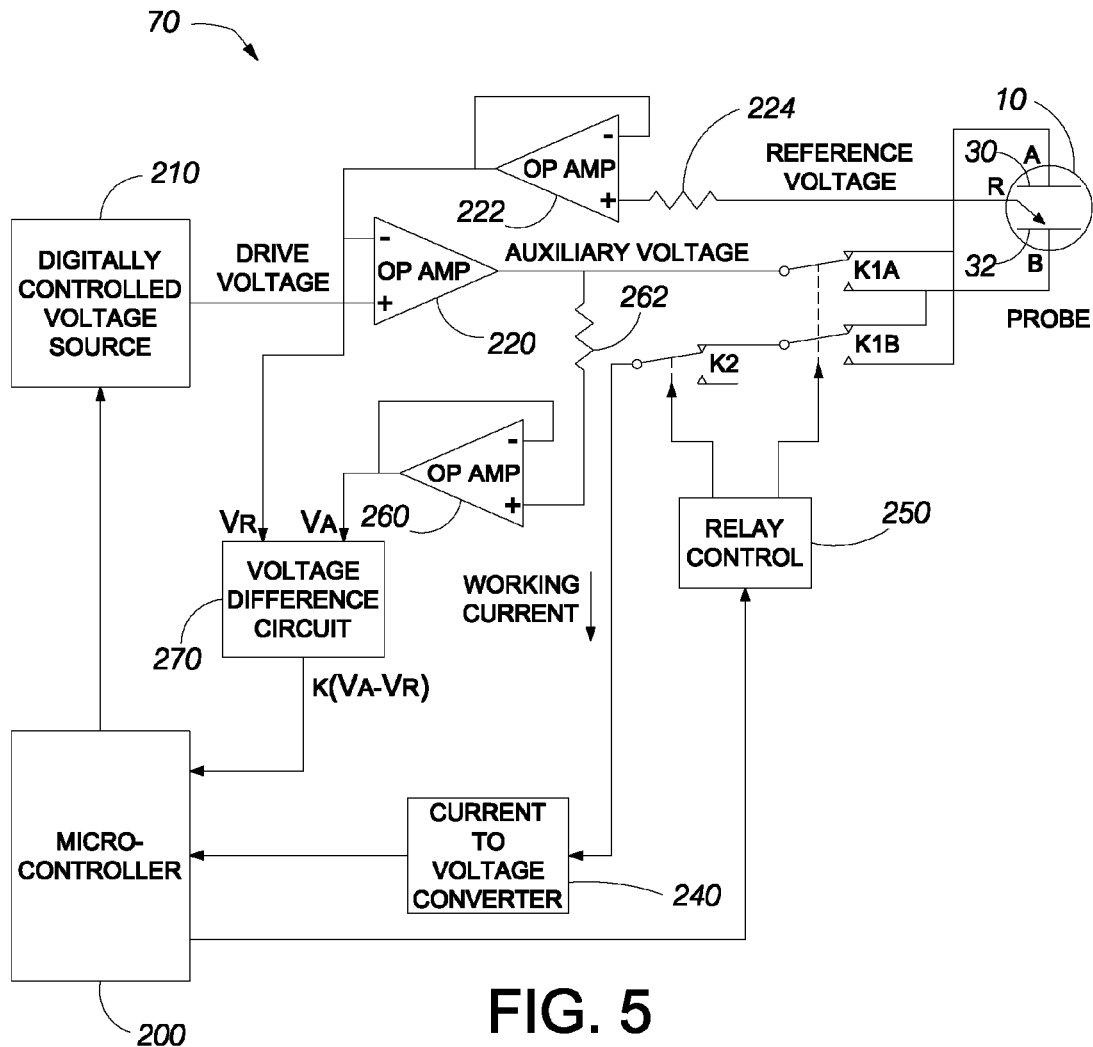
FIG. 5 illustrates a schematic diagram of a portion of the control circuitry for the probe of FIGS. 1-4.

FIG. 5 illustrates a partial schematic diagram of the control circuitry 70 to show the portion of the control circuitry that controls the operation of the chlorine measurement system disclosed herein. A microcontroller 200 controls the circuitry show in FIG. 5 as well as other circuitry not shown. With respect to the chlorine measurement system, the microcontroller 200 sends control signals to a digitally controlled voltage source 210, which advantageously comprises a programmable potentiometer, such as, for example, an AD5242 256-position digital potentiometer commercially available from Analog Devices. In the illustrated embodiment, the microcontroller 200 communicates with the programmable voltage source 210 via the serial data and serial clock lines of a conventional I²C bus.

The output of the digitally controlled voltage source 210 is an analog drive voltage that varies around a fixed sensor virtual ground voltage, which is set to one-half the system supply voltage (e.g., 2.5 volts when the system supply voltage is 5.0 volts). When measuring chlorine, as described below, the drive voltage is set to approximately 0.2 volts below the sensor virtual ground voltage (e.g., at −0.2 volts with respect to the sensor virtual ground voltage).

The drive voltage is provided as the input to the non-inverting (+) input of a first operational amplifier (OP AMP) 220. The inverting (−) input of the first operational amplifier 220 is connected to the output of a second operational amplifier 222. The second operational amplifier 222 is configured as a unity amplification voltage follower by connecting the output to the inverting (−) input. The non-inverting (+) input of the second operational amplifier 222 is connected to the reference electrode (R) of the sensor (PROBE) 10 via a resistor 224. As discussed above, the reference electrode (R) may be the reference electrode of the pH sensor 20, if used in the system, or the reference electrode (R) may be a separate electrode positioned in the sensor tip 16.

The output of the first operational amplifier 220 is an auxiliary voltage or counter voltage that is applied to the auxiliary electrode of the sensor 10; however, unlike conventional sensor systems, the auxiliary voltage is not applied to a particular electrode of the sensor 10. Rather, the auxiliary voltage is applied to the common pole of a first set of contacts K1A of a double-pole, double throw relay. The normally closed (upper) contact of the first set of contacts K1A is connected to a terminal A of the sensor 10, which is connected to the first electrode 30 described above. The normally open (lower) contact of the first set of contacts K1A is connected to a terminal B of the sensor 10, which is connected to the second electrode 32 described above.

The first set of contacts K1A are controlled in common with a second set of contacts K1B. As illustrated, the normally closed (upper) contact of the second set of contacts K1B is connected to the normally open (lower) contact of the first set of contacts K1A and thus is connected to the second electrode 32 via the terminal B of the sensor 10. The normally open (lower) contact of the second set of contacts K1B is connected to the normally closed (upper) contact of the first set of contacts K1A and thus is connected to the first electrode 30 via the terminal A of the sensor 10.

The common pole of the second set of contacts K1B is connected to the normally closed (upper) contact of a second relay K2. The normally open (lower) contact of the second relay K2 is not connected. The common pole of the second relay K2 is connected to an input of a current to voltage converter 240. The output of the current to voltage converter 240 is an analog voltage that represents the magnitude of the input current. The analog voltage from the current to voltage converter 240 is applied to an analog input of the microcontroller 200. An analog-to-digital converter incorporated in the microcontroller 200 converts the analog voltage to a digital representation of the current into the current to voltage converter 240.

The first set of contacts K1A and the second set of contacts K1B are controlled by a first output of the relay control circuit 250, which is controlled by the microcontroller 200. For example, when the first output of the relay control circuit 250 is high, the common pole of each set of contacts K1A, K1B is coupled to the normally closed (upper) contact. When the first output of the relay control circuit 250 is low, the common pole of each set of contacts K1A, K1B is coupled to the normally open (lower) contact.

The second relay K2 is controlled by a second output of the relay control circuit 250 in a similar manner. When the system is measuring chlorine, the second relay K2 is controlled so that the common pole is connected to the normally closed (upper) contact so that the common pole of the second set of contacts K1B of the first relay K1 is electrically connected to the input of the current to voltage converter 240.

The first operational amplifier 220, the second operational amplifier 222 and the electrodes of the sensor 10 operate as a potentiostat having two different configurations determined by the state of the two sets of contracts K1A, K1B. In particular, in a first configuration, when the control voltage from the relay control circuit 250 is high, the two sets of contacts are in the normally closed position with the respective common poles connected to the respective upper contacts. In the first configuration, the auxiliary voltage produced by the first operational amplifier 220 is applied to the first electrode 30 via the upper contact of the first set of contacts K1A and the terminal A. Accordingly, the first electrode 30 is the auxiliary or counter electrode in the first configuration. The second electrode 32 is electrically connected via the terminal B, the upper contact of the second set of contacts K1B and the second relay K2 to the input of the current to voltage converter 240. Accordingly, the second electrode 32 is the working electrode in the first configuration.

In the first configuration, the auxiliary voltage is applied to the first electrode 30 and the voltage on the reference electrode is applied to the second operational amplifier 222. The second operational amplifier 222 buffers the reference voltage and applies the corresponding voltage to the inverting (−) input of the first operational amplifier 220. The first operational amplifier 222 varies the auxiliary voltage as required to maintain the reference voltage at the same level as the drive voltage applied to the non-inverting (+) input. The variations in the auxiliary voltage cause variations in the current flowing out of the second electrode 32 (the working electrode in this configuration) and into the current to voltage converter 240. As discussed above, the current is converted to an analog voltage applied to the analog input of the microcontroller 200, which digitizes the voltage. The microcontroller processes the resulting digital data to determine the chlorine concentration from the measured current value.

In a second configuration of the potentiostat, when the control voltage from the relay control circuit 250 is low, the two sets of contacts are switched to the normally open position with the respective common poles connected to the respective lower contacts. In the second configuration, the auxiliary voltage produced by the first operational amplifier 220 is applied to the second electrode 32 via the lower contact of the first set of contacts K1A and the terminal B. Accordingly, the second electrode 32 is the auxiliary or counter electrode in the second configuration. The first electrode 30 is electrically connected via the terminal A, the lower contact of the second set of contacts K1B and the second relay K2 to the input of the current to voltage converter 240. Accordingly, the first electrode 30 is the working electrode in the second configuration.

In the second configuration, the auxiliary voltage is applied to the second electrode 32. The voltage on the reference electrode is applied to the second operational amplifier 222 as discussed above. The second operational amplifier 222 buffers the reference voltage and applies the corresponding voltage to the inverting (−) input of the first operational amplifier 220. The first operational amplifier 222 varies the auxiliary voltage as required to maintain the reference voltage at the same level as the drive voltage applied to the non-inverting (+) input. The variations in the auxiliary voltage cause variations in the current flowing out of the first electrode 30 (the working electrode in this configuration) and into the current to voltage converter 240. As discussed above, the current is converted to an analog voltage applied to the analog input of the microcontroller 200, which digitizes the voltage. The microcontroller processes the resulting digital data to determine the chlorine concentration from the measured current value.

Figure 6:
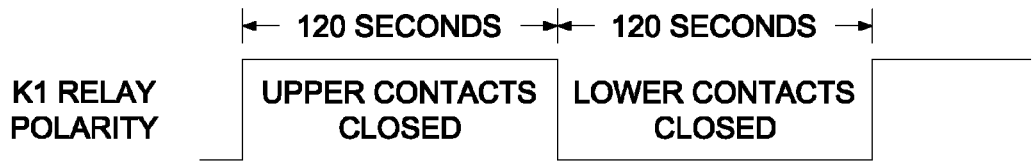
FIG. 6 illustrates a timing diagram for the switching of the relay contacts that control the alternating connection of the two electrodes in FIG. 5 as the auxiliary electrode and the working electrode.

As illustrated in FIG. 6, in the preferred embodiment, the microcontroller 200 controls the relay control circuit 250 to cause the polarity of the first relay K1 to switch every 120 seconds. The chlorine concentration is measured during each 120-second interval and stored within memory in the microcontroller 200. The measured chlorine concentrations over multiple intervals are advantageously averaged (e.g., via a moving window averaging method) to determine the chlorine concentration. Furthermore, the measured chlorine concentrations in the two configurations are compared to determine whether the two measurements are substantially different. A substantial difference in the measured chlorine concentrations in the two configurations may indicate a failing electrode or other problems in the system. For example, an error may be indicated when a difference between the first signal and the second signal is more than 10% of the magnitude of one of the signals. Since the working electrode is constantly switched in the embodiments disclosed herein, the reading from one electrode when electrically positioned as the working electrode is compared with the reading from the other electrode when electrically positioned as the working electrode to ensure that the reading is reliable.

As discussed above, the control voltage applied to the second relay K2 can be changed to open the normally closed (upper) contact and close the normally open (lower) contact to disconnect the currently selected working electrode from the input of the current to voltage converter 240. Accordingly, no current flows out of the working electrode. When the system is in this configuration, the voltage between the currently selected auxiliary electrode and the reference electrode can be measured to determine whether the voltage is within a predetermined range. In the illustrated embodiment, a third operational amplifier 260 configured as a voltage follower buffers the auxiliary voltage from the first operational amplifier 220 via a resistor 262. The output of the third operational amplifier 260 is a buffered auxiliary voltage ($V_A$) is coupled to a first input of a voltage difference circuit 270. A second input of the voltage difference circuit 270 is connected to the output of the second operational amplifier 222 to receive the buffered reference voltage ($V_R$). The voltage difference circuit 270 comprised a plurality of operational amplifiers configured to produce an output voltage that is proportional to the difference between the two input voltages (e.g., $K(V_A-V_R)$). For example, in the illustrated embodiment, $K$ is 4. The voltage difference represents the oxidation reduction potential (ORP) between the auxiliary electrode and the reference electrode. This measurement of the oxidation reduction potential between the two electrodes verifies that the chlorine concentration reading is accurate and provides a redundant "second opinion." The integrated ORP measurement also serves as an additional water quality indicator. The operation of the sensor ensures that problems related to conventional passive ORP systems due to electrode poisoning will not affect this system. Monitoring of the voltage on the auxiliary with respect to the voltage on the reference electrode also ensures that failure modes such as a faulty reference electrode will be detected by the system.

The system and method disclosed herein have many advantages. For example, by continuously changing the electrical positions of the two electrodes on alternating cycles, any salts that migrate toward one electrode during one cycle are immediately released during the next cycle to prevent the salts from nucleating on the electrode. Accordingly, scale buildup is prevented and other effects of polarization on the working electrode are avoided. The salts are released without apply damaging potentials to the electrode. Ultrasonic cleaning can be applied to all the electrodes to minimize biofouling or scaling, which cleans the reference electrode as well as the measurement electrodes. Auto-scaling of the potentiostat enables the potentiostat to measure with either high accuracy or high levels by automatically scaling the signal sensitivity.

Integrated conductivity measurement can also be used to detect whether air is present in the sensor by varying the drive voltage about a selected nominal drive voltage and measuring the current flowing from the working electrode.

The present invention is disclosed herein in terms of a preferred embodiment thereof as defined in the appended claims. Various changes, modifications, and alterations in the teachings of the present invention may be contemplated by those skilled in the art without departing from the intended spirit and scope of the appended claims. It is intended that the present invention encompass such changes and modifications.

I claim:

1. A sensor that performs conductivity measurement, amperometric chlorine or bromine measurement and measurement of oxidation reduction potential of water in a water system, the sensor comprising:
- no more than three electrodes, including a first electrode and a second electrode and a reference electrode;
- an auxiliary voltage circuit that generates an auxiliary voltage in accordance with a selected one of a conductivity measurement, an amperometric chlorine or bromine measurement and an oxidation reduction potential measurement to be performed;
- a voltage difference circuit;
- a current to voltage converter; and
- a control circuit that selectively configures the first and second electrode in one of a first configuration and a second configuration to measure amperometric chlorine or bromine in the first configuration and to measure oxidation reduction potential in the second configuration, wherein:
  - in the first configuration, one of the first and second electrodes is connected to the auxiliary voltage circuit and the other of the first and second electrodes is connected to the current to voltage converter to enable measurement of chlorine or bromine concentration and to enable measurement of conductivity; and
  - in the second configuration, one of the of the first and second electrodes is connected to the auxiliary voltage circuit and the other of the first and second electrodes is unconnected, the auxiliary voltage and a voltage from the reference electrode being provided to the voltage difference circuit to enable measurement of oxidation reduction potential.

* * * * *